United States Patent
Bonnette et al.

(10) Patent No.: US 9,737,328 B2
(45) Date of Patent: Aug. 22, 2017

(54) HYDRODYNAMIC ECCENTRICALLY PIVOTING CATHETER

(71) Applicant: Boston Scientific Limited, Hamilton (BM)

(72) Inventors: Michael J. Bonnette, Minneapolis, MN (US); Hieu V. Le, Brooklyn Park, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 531 days.

(21) Appl. No.: 13/830,699

(22) Filed: Mar. 14, 2013

(65) Prior Publication Data

US 2014/0277007 A1  Sep. 18, 2014

(51) Int. Cl.
*A61B 17/3203* (2006.01)
*A61B 17/22* (2006.01)
*A61F 2/01* (2006.01)

(52) U.S. Cl.
CPC .......... *A61B 17/32037* (2013.01); *A61B 2017/22039* (2013.01); *A61B 2017/22041* (2013.01); *A61B 2017/22079* (2013.01); *A61F 2/013* (2013.01); *A61F 2002/016* (2013.01)

(58) Field of Classification Search
CPC ......... A61B 17/20; A61B 17/22; A61B 17/32; A61B 18/14; A61B 17/32037; A61B 2017/22039; A61M 25/14; A61M 29/02; A61M 2025/0183; A61M 25/0052; A61M 25/0029; A61F 2/013; A61F 2002/016
USPC ........................................................ 606/159
See application file for complete search history.

(56) References Cited

U.S. PATENT DOCUMENTS

| | | | |
|---|---|---|---|
| 5,704,926 | A | 1/1998 | Sutton |
| 5,711,909 | A | 1/1998 | Gore et al. |
| 6,676,627 | B1 | 1/2004 | Bonnette et al. |
| 6,676,637 | B1 | 1/2004 | Bonnette et al. |
| 6,755,803 | B1 | 6/2004 | Le et al. |
| 6,875,193 | B1 | 4/2005 | Bonnette et al. |
| 7,031,290 | B2 | 4/2006 | Ertel et al. |

(Continued)

FOREIGN PATENT DOCUMENTS

| | | |
|---|---|---|
| EP | 1382366 B1 | 1/2004 |
| WO | 0069348 A1 | 11/2000 |

(Continued)

OTHER PUBLICATIONS

International Search Report and Written Opinion of corresponding PCT Application No. PCT/US2014/022511 filed on Mar. 10, 2014.

*Primary Examiner* — Eric Rosen
*Assistant Examiner* — George J Ulsh
(74) *Attorney, Agent, or Firm* — Seager, Tufte & Wickhem, LLP

(57) ABSTRACT

A hydrodynamic catheter includes a catheter body with a catheter lumen and an infusion tube extending within the catheter body, the infusion tube configured for coupling with a fluid source near the catheter proximal portion. An inflow orifice and an outflow orifice are positioned at locations along a catheter body perimeter. A fluid jet emanator is in fluid communication with the infusion tube, where the fluid jet emanator includes one or more jet orifices configured to direct one or more fluid jets through the catheter lumen from near the inflow orifice toward the outflow orifice. A pivot cylinder located along the catheter body perimeter is positioned distal relative to one or more of the fluid jet emanator, the inflow orifice, or the outflow orifice.

9 Claims, 10 Drawing Sheets

(56) References Cited

U.S. PATENT DOCUMENTS

| | | |
|---|---|---|
| 7,897,022 B2 | 3/2011 | Simmons et al. |
| 7,935,077 B2 | 5/2011 | Thor et al. |
| 8,398,579 B2 | 3/2013 | Morris et al. |
| 2005/0059957 A1 | 3/2005 | Campbell et al. |
| 2006/0012909 A1 | 1/2006 | Zayas et al. |
| 2006/0064123 A1 | 3/2006 | Bonnette et al. |
| 2008/0275393 A1 | 11/2008 | Bonnette et al. |
| 2008/0300532 A1 | 12/2008 | Bonnette et al. |
| 2009/0018565 A1 | 1/2009 | To et al. |
| 2010/0145259 A1 | 6/2010 | Nash et al. |
| 2010/0312223 A1 | 12/2010 | Kozak et al. |
| 2011/0015564 A1 | 1/2011 | Bonnette et al. |

FOREIGN PATENT DOCUMENTS

| | | |
|---|---|---|
| WO | 03000316 A1 | 1/2003 |
| WO | 2004064891 A2 | 8/2004 |
| WO | 2005023354 | 3/2005 |

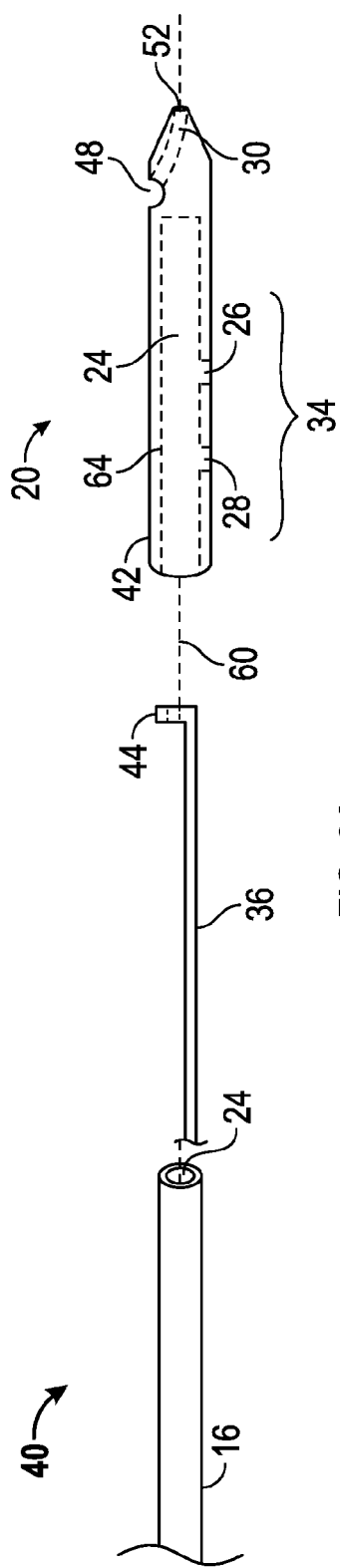
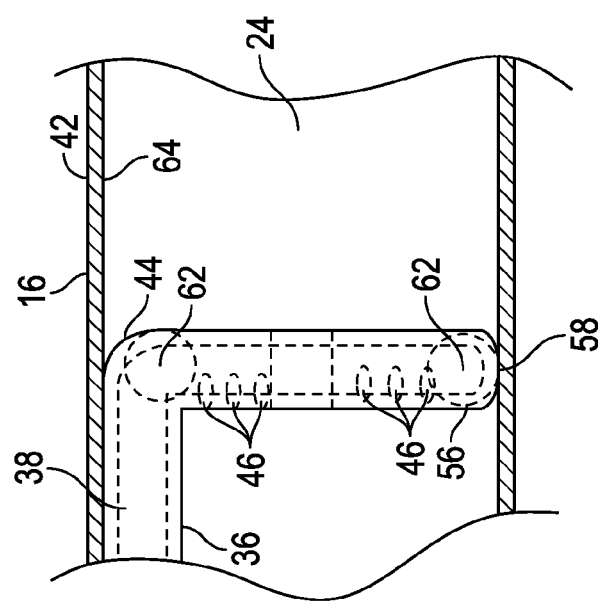
FIG. 2A
FIG. 2B

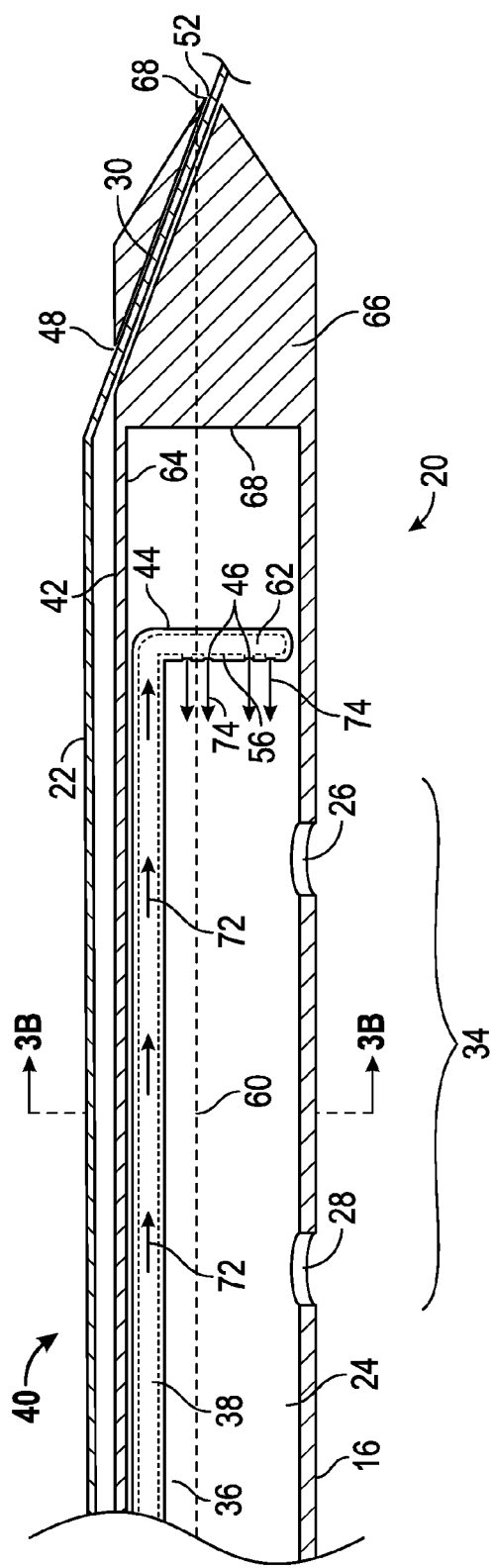
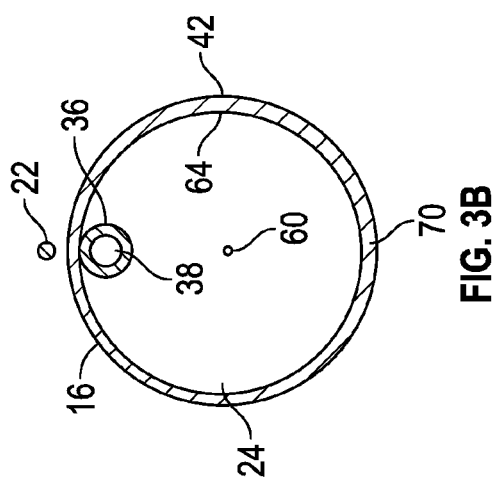
FIG. 3A
FIG. 3B

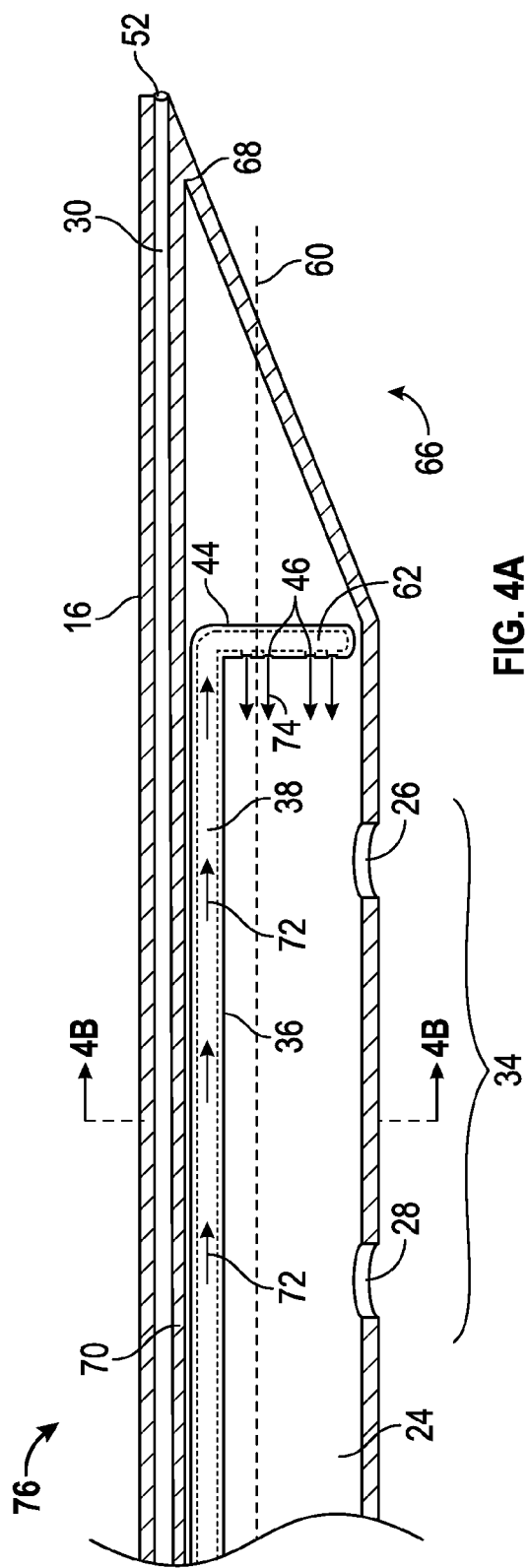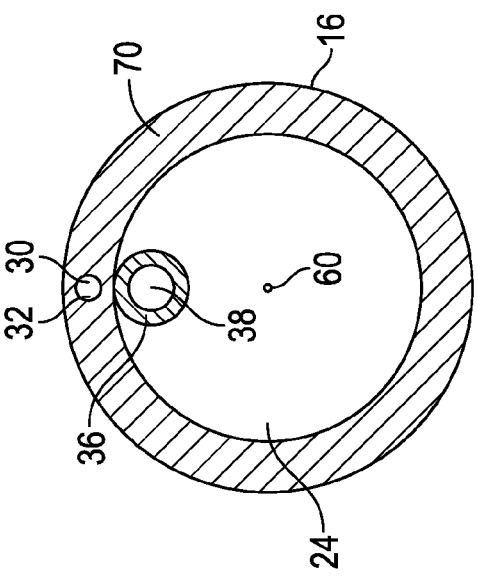
FIG. 4A
FIG. 4B

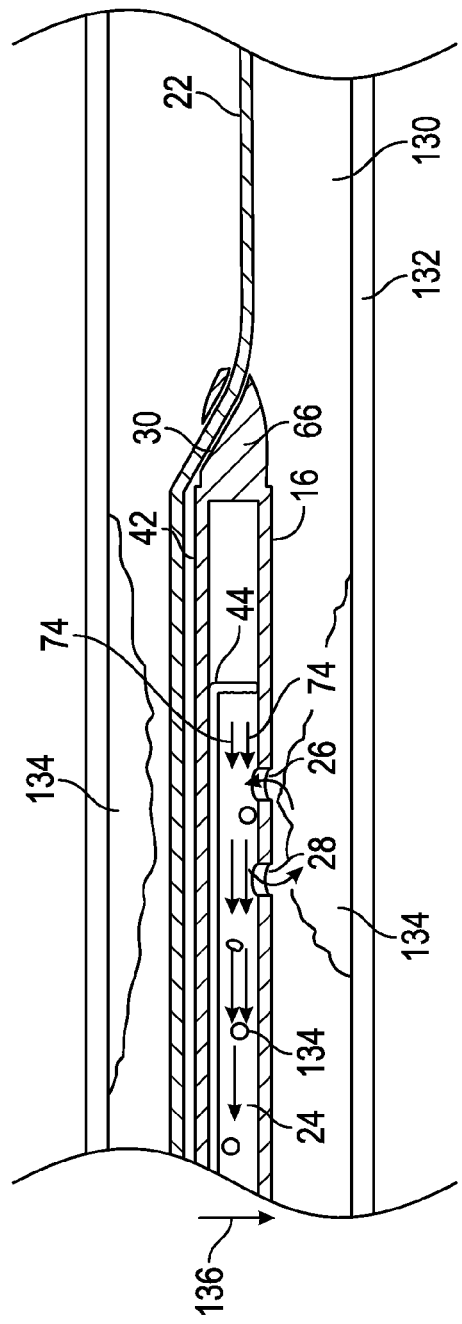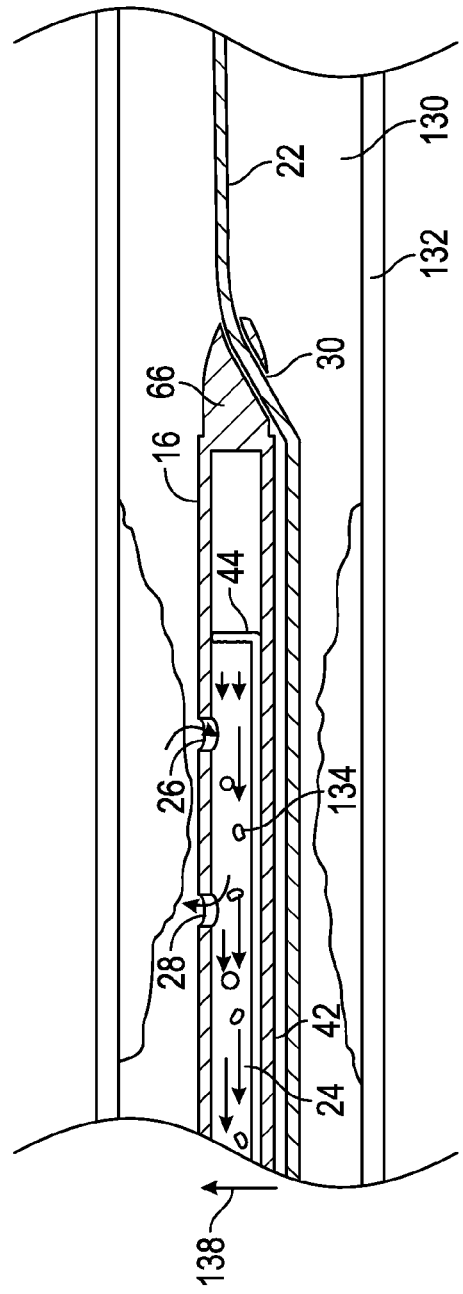

HYDRODYNAMIC ECCENTRICALLY PIVOTING CATHETER

TECHNICAL FIELD

This document pertains generally to medical devices, and more specifically to hydrodynamic catheters and systems.

BACKGROUND

Thrombectomy is a medical procedure that removes a blood clot (e.g., thrombus) from a vessel, such as an artery or vein. Left untreated thrombus may occlude a vessel or break free and preclude blood flow to one or more organs.

One technique to perform a thrombectomy includes a catheter having an infusion lumen that delivers lytic solutions that can breakdown or dissolve the thrombus. The catheter or a second catheter includes an aspiration lumen that aspirates the broken down or dissolved thrombus particulate.

Thrombectomy devices (e.g., thrombectomy catheters) can use fluid jet streams to ablate thrombus. In an example, a catheter used during a thrombectomy procedure is fed over a guidewire such that the catheter is concentric with the guidewire. In that instance, the catheter body performing the thrombectomy is positioned within a lumen of the catheter. In order to facilitate delivery and navigate through vasculature of a patient, the diameter of the catheter is relatively small compared to a vessel being treated. The catheter provides a treatment delivery footprint within the vessel that is equal to the diameter of the catheter body (e.g., as the guidewire is coincident with the guidewire).

OVERVIEW

The present inventors have recognized, among other things, that a problem to be solved includes increasing a treatment delivery footprint of a catheter body (e.g., a hydrodynamic catheter used to perform a thrombectomy procedure) within a vessel without increasing the diameter of the catheter body. Increasing the treatment delivery footprint of the catheter body (e.g., the proximity of the treatment features of a catheter to the targeted thrombus) increases the efficiency of the thrombectomy procedure while maintaining a minimal catheter perimeter minimizing damage to the vessel. Additionally, another problem to be solved includes the removal of structural obstructions within a catheter lumen, for instance an infusion lumen or aspiration lumen. Removing structural obstructions from the catheter interior, especially while maintaining a relatively small catheter perimeter, increases the area available for energy transfer (e.g., the maintenance of delivery pressure and aspirating pressure between the catheter proximal and distal ends).

Existing thrombectomy devices (e.g., a catheter) can include a guidewire that is concentric with a lumen of the catheter. Therefore, rotation of the catheter about the guidewire provides a footprint within the vessel that is equal to the diameter of the catheter body. As the thrombectomy procedure continues and the thrombus is broken down, the existing devices can be inefficient at obtaining intimate contact between the thrombus and an inlet and outlet orifice of the catheter. Additionally, having the guidewire positioned in the path of the indirect cross-path fluid jet streams can diminish and or decrease the strength of the thrombectomy procedure, thereby decreasing the effectiveness of the procedure.

The present subject matter provides a solution to these problems, by providing a hydrodynamic catheter and system that provides a treatment delivery footprint of the catheter within a vessel that is larger than the actual diameter of the catheter. The larger treatment delivery footprint of the hydrodynamic catheter described herein in effect creates a virtual perimeter for the treatment features of the catheter larger than perimeter of the catheter. In an example, a guidewire extends along a catheter body external surface at least between the inflow and outflow orifice (e.g., the treatment features of the catheter). Providing the guidewire along the catheter body external surface provides the catheter body to be eccentric in its path of travel as the device is rotated about the guidewire. Thus, the treatment delivery footprint of the catheter body within the vessel is increased as compared to a guidewire positioned concentrically with a catheter body having an equal diameter. For example, the portions of the catheter positioned opposite of the guidewire and guidewire lumen, when rotated, are moved into intimate proximity relative to the vessel wall. Accordingly, any catheter treatment features provided at those portions are similarly positioned in intimate proximity to the thrombus and vessel wall. In an example using the catheter for a thrombectomy including introducing fluid jets (e.g., of lytic solution) allows for the penetrating delivery of the fluid into the thrombus interior as opposed to the exterior where it may quickly dilute or flow downstream.

Additionally, the present subject matter clears the catheter lumen from structural obstructions (e.g., a guidewire) between at least inflow and outflow orifices. Energy (e.g., the maintenance of pressurization in the delivery fluid) is conserved allowing enhanced thrombectomy procedures, for instance by high pressure delivery and aspiration of fluids and entrained particulate from the area of interest in the vessel. For example, by removing the guidewire from the catheter lumen, at least between the inflow and outflow orifices, the area within the catheter lumen available for energy transfer increases thereby also increasing the efficiency of the device while maintaining a relatively small catheter perimeter, as compared to the vessel.

In an example, the present subject matter provides a hydrodynamic catheter for use in a thrombectomy procedure. The hydrodynamic catheter includes a catheter body with a catheter lumen extending from a proximal catheter portion to a distal catheter portion. The hydrodynamic catheter includes an inflow orifice at a first location along a catheter body perimeter and an outflow orifice at a second location along the catheter body perimeter spaced from the first location. A fluid jet emanator includes one or more jet orifices configured to direct one or more fluid jets through the catheter lumen from near the inflow orifice toward the outflow orifice. The hydrodynamic catheter includes a pivot cylinder at a third location along the catheter body perimeter, the third location distal relative to one or more of the fluid jet emanator, the inflow orifice, or the outflow orifice. At least a portion of the catheter body including the inflow and outflow orifices is rotatable around the pivot cylinder between at least first and second rotated positions. In the first rotated position the inflow and outflow orifices are directed in a first direction, and the inflow and outflow orifices are positioned in close proximity to a first portion of a vessel. In the second rotated position the inflow and outflow orifices are directed in a second direction different from the first direction, and the inflow and outflow orifices are positioned in close proximity to a second portion of a vessel different from the first portion of the vessel.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2A illustrates an exploded view of a hydrodynamic catheter, in accordance with one embodiment of the present disclosure.

FIG. 2B illustrates a close-up view of a fluid emanator positioned within the catheter body illustrated in FIG. 2A.

FIG. 3A illustrates a partial cross-section of the hydrodynamic catheter in FIGS. 1 and 2.

FIG. 3B illustrates a cross-section of the hydrodynamic catheter in FIG. 3A along lines 3B-3B.

FIG. 4A illustrates a partial cross-section of another example of a hydrodynamic catheter, in accordance with one embodiment of the present disclosure.

FIG. 4B illustrates a cross-section of the hydrodynamic catheter in FIG. 4A along lines 4B-4B.

FIG. 11A illustrates a partial cross-section of the hydrodynamic catheter in FIG. 3A within a vessel at a first rotated position.

FIG. 11B illustrates a partial cross-section of the hydrodynamic catheter in FIG. 3A within a vessel at a second rotated position.

DETAILED DESCRIPTION

Figure 1:
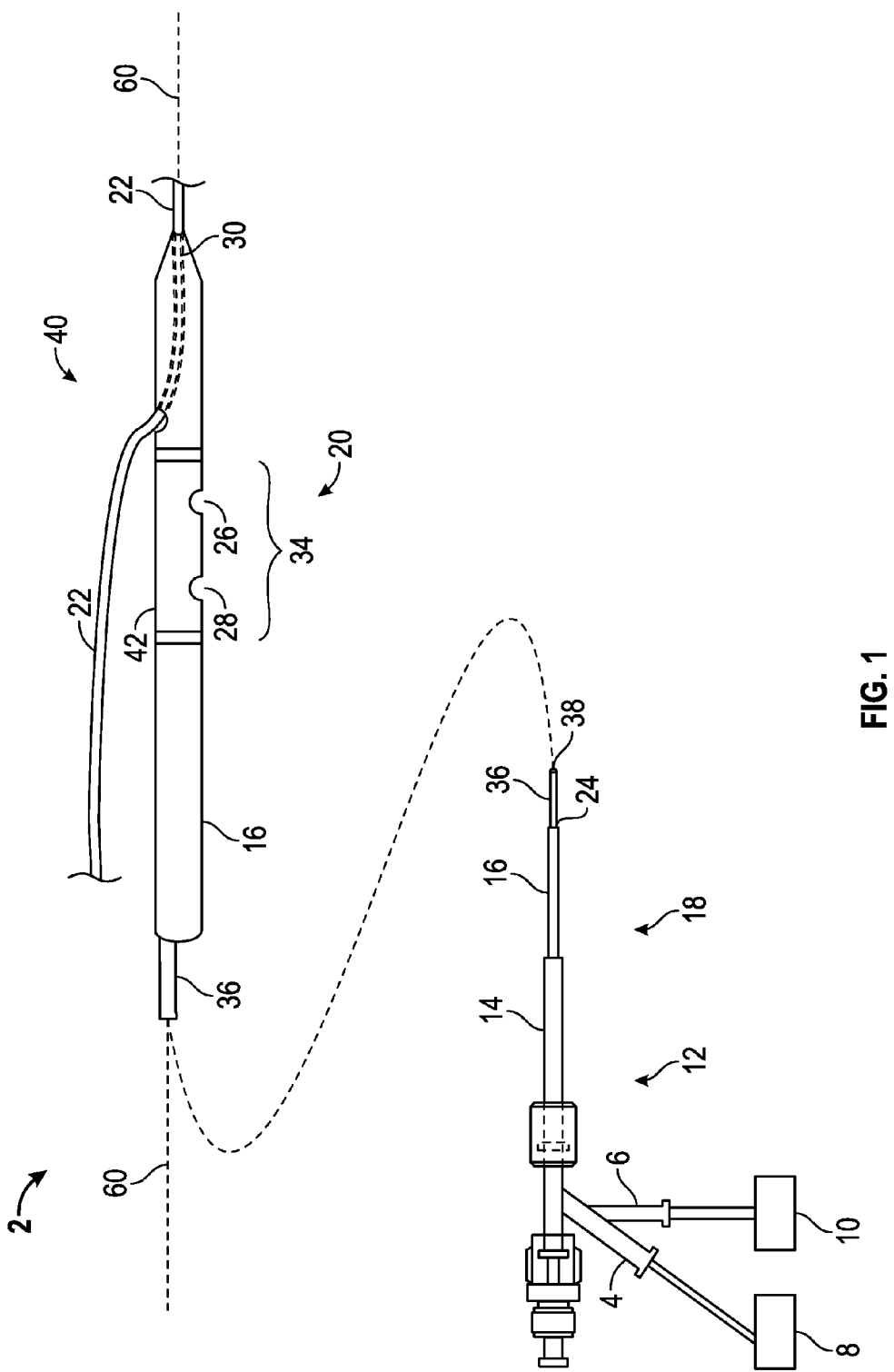
FIG. 1 illustrates a hydrodynamic catheter system, in accordance with one embodiment of the present disclosure.

FIG. 1 illustrates a hydrodynamic catheter system 2, in accordance with one embodiment of the present disclosure. As will be described in detail herein, the hydrodynamic catheter system 2 is configured to provide a pressurized fluid at a catheter distal portion 20 for removal of thrombus from a vessel. Additionally, the hydrodynamic catheter system 2 is optionally configured to provide a vacuum source (aspiration) at the catheter distal portion 20 for removal of thrombus with the pressurized fluid.

In an example, the hydrodynamic catheter system 2 includes a hydrodynamic catheter 40 in association with a manifold 18. The hydrodynamic catheter 40 is coupled to and extends distally from the manifold 18. The hydrodynamic catheter 40 includes a catheter body 16 having a catheter lumen 24 extending along a length of the catheter body 16 (e.g., from a catheter proximal portion 18 to a catheter distal portion 20). The hydrodynamic catheter 40 also includes an infusion tube 36 including an infusion lumen 38 extending along a length of the catheter lumen 24. The infusion tube 36 extends within the catheter body 16 from a catheter proximal portion 18 towards the catheter distal portion 20 and is configured to deliver fluid under pressure to the catheter distal portion 20 for removal of thrombus.

The hydrodynamic catheter 40 includes a treatment portion 34 positioned along a portion of the catheter body 16. In an example, the catheter distal portion 20 includes the treatment portion 34. The treatment portion 34 includes at least one inflow orifice 26 and at least one outflow orifice 28. In an example, the inflow and outflow orifices 26, 28 cooperate with fluid jets to provide a cross stream effect where fluid is projected from the catheter body 16 through the outflow orifice 28 and is recirculated to the catheter body 26 through the inflow orifice 26. The fluid entering and exiting the catheter body 16 thereby develops a circular or cross stream flow that engages with thrombus within a vessel, dislodges and macerates the thrombus, and entrains the thrombus particles in the fluid flow returned to the catheter body 16 through the inflow orifice 26.

In an example, the infusion tube 36 is coupled to an injection side port 6 such that the infusion lumen 38 is coupled to a fluid delivery device 10, such as an injector or pumping device. The infusion lumen 38 delivers fluid under pressure to the catheter distal portion 20, for example, to a jet orifice used in a thrombectomy procedure. In one example, the jet orifice provides a fluid jet at pressures of around 1500 pounds per square inch (psi) for hydrodynamic engagement with thrombus (although other pressures may be obtained with the same or differing fluid delivery devices 10). As illustrated in FIG. 1, the hydrodynamic catheter system 2 includes a strain relief fitting 14 coupled between to the catheter body 16 (at the catheter proximal portion 18) and the manifold 18. In an example, the strain relief fitting 14 extends around the catheter body 16 and is engaged with the manifold 18. In another example, the catheter lumen 24 communicates with an aspiration side port 4 that is coupled to an aspirator 8, such as a vacuum source. The vacuum source includes, but is not limited to, a syringe, vacuum bottle, roller pump, vacuum pump or the like.

The hydrodynamic catheter 40 includes a pivot cylinder 30. In an example, the pivot cylinder 30 is adjacent to the treatment portion 34. The pivot cylinder 30 is eccentric relative to a longitudinal axis 60 of the hydrodynamic catheter 40. As illustrated in FIG. 1, the pivot cylinder 30 is positioned along the catheter distal portion 20 at a position that is distal relative to one or more of the fluid jet emanator 44 (as illustrated in FIG. 2), the inflow orifice 26, or the outflow orifice 28. In an example, the treatment portion 34 is positioned proximal relative to the pivot cylinder 30 and is rotatable around the pivot cylinder 30 between at least a first rotated positioned and a second rotated position. In one example, the pivot cylinder 30 can include, but is not limited to a guidewire lumen extending therein that is configured to receive a guidewire 22. The treatment portion 34 of the catheter body 16 is rotatable around the pivot cylinder 30, in one example 360 degrees. In an example, the guidewire 22 is positioned through the guidewire lumen of the pivot cylinder 30 and along a catheter body external surface 42 along at least the treatment portion 34. Providing the guidewire 22 along the catheter body external surface 42 positions the catheter body 16 eccentrically relative to the guidewire 22 and the pivot cylinder 30 in a rotating path of travel as the hydrodynamic catheter 40 rotates about the guidewire 22.

By rotating the treatment portion 34 of the catheter body 34 about the pivot cylinder 30, the portions of the catheter positioned opposite of the guidewire 22 are moved into intimate proximity relative to the vessel wall. Accordingly, any catheter treatment features (e.g, the inlet and outlet orifices 26, 28) are similarly positioned in intimate proximity to the thrombus and vessel wall. As the catheter body 16 rotates about the guidewire 22, a treatment delivery footprint creates a virtual perimeter for the treatment features that is greater than a perimeter of the catheter body 16. The eccentric positioning of the pivot cylinder relative to the longitudinal axis increases the treatment delivery footprint while maintaining a minimal actual catheter perimeter that is more easily delivered and navigated through the vasculature. Furthermore, positioning the guidewire 22 along the catheter body external surface 42 at least between the inflow and outflow orifices 26, 28, clears the catheter lumen 24 from structural obstructions (e.g., a guidewire 22) between at least the inflow and outflow orifices 26, 28 and thereby conserves energy (fluid velocity and pressure) and provides enhanced thrombectomy effectiveness.

In operation, the hydrodynamic catheter 40 is inserted into a vessel, such as a vein or artery, and fluid is delivered to the catheter distal portion 20 via the infusion lumen 38. The fluid is delivered through one or more fluid jets and hydrodynamically engages and dislodges thrombus within the vessel (e.g., through concentrated fluid pressure, fluid velocity, and fluid flow volume). For instance, the one or more fluid jets provided through the outflow orifice 28 (or orifices) impact the thrombus and mechanically macerate the thrombus. As discussed herein, the catheter lumen 24 receives the dislodged thrombus particulate, through the inlet orifice 26, and delivers the thrombus particulate along the catheter lumen 24 through an aspiration side port 4 to a waste unit such as a collection bag, vial, chute and the like.

FIG. 2A illustrates an exploded view of a hydrodynamic catheter 40, in accordance with one embodiment of the present disclosure. As illustrated in FIG. 2B, the infusion tube 36 is in fluid communication with a fluid jet emanator 44. The catheter body 16 includes the treatment portion 34 positioned at the catheter distal portion 20. The treatment portion 34 includes the inflow and outflow orifices 26, 28 that are in fluid communication with the catheter lumen 24. As discussed herein, the inflow and outflow orifices 26, 28 generate a cross stream flow that removes deposited thrombus within a vessel. In an example, the catheter body 16 includes radiopaque collars positioned on each side of the treatment portion 34. That is, a first radiopaque collar is positioned adjacent to the inflow orifice 26 and a second radiopaque collar is positioned adjacent to the outflow orifice 28. The radiopaque collars assist with imaging of the catheter distal portion 20 during insertion and navigation through a vessel, under fluoroscopic viewing.

The pivot cylinder 30 includes a pivot cylinder inlet 48 and a pivot cylinder outlet 52. In an example, the pivot cylinder outlet 52 is in a non-parallel orientation (e.g., is angled) to the pivot cylinder inlet (or 48. In one example, the pivot cylinder outlet 52 is substantially perpendicular to the pivot cylinder inlet 48. In an example, the pivot cylinder includes a guidewire lumen, such that a guidewire can be positioned through the guidewire lumen. For example, the guidewire lumen extends between the pivot cylinder inlet 48 and the pivot cylinder outlet 52 and a guidewire inlet can correspond to the pivot cylinder inlet 48 and a guidewire outlet can correspond to a pivot cylinder outlet 52. The pivot cylinder 30 and corresponding guidewire lumen are eccentric relative to the longitudinal axis 60 of the hydrodynamic catheter 40 (e.g., non-coincident or spaced from the longitudinal axis 60).

As illustrated in FIG. 2A, the pivot cylinder inlet 48 is radially spaced around the catheter body 16 from the inflow orifice 26 and the outflow orifice 28. In one example, the portions of the catheter body 16 positioned opposite of pivot cylinder 30 (e.g., the treatment portion 34 including the inlet and outlet orifices 26, 28), when rotated, are moved into intimate proximity relative to the vessel wall. Positioning the treatment portion 34 opposite the pivot cylinder inlet 48 ensures that the largest treatment delivery footprint is created during operation. For example, the inlet and outlet orifices 26, 28 are positioned in intimate proximity to the thrombus and vessel wall when the catheter body 16 is rotated about the pivot cylinder 30. As discussed herein, a diameter of the treatment delivery footprint is greater than a diameter of the catheter body 16. Thus, the hydrodynamic catheter 40 including the pivot cylinder 30 increases the effectiveness of thrombectomy (e.g., by positioning the treatment portion 34 of the hydrodynamic catheter 40 in intimate contact with thrombus and the vessel wall) without increasing the size (e.g., diameter) the hydrodynamic catheter 40.

In an example, the catheter body 16 has a diameter within a range of from about 3 French (Fr) to about 8 Fr and uses a 0.014 inch to a 0.035 inch guidewire for insertion. In another example, the catheter body 16 has a diameter within a range of from about 6 Fr to about 8 Fr and is inserted using a 0.035 inch guidewire. In yet another example, the catheter body 16 has a diameter within a range of from about 5 Fr to about 6 Fr and is inserted using a 0.018 inch guidewire Optionally, the catheter body 16 includes other diameters and is accordingly usable with corresponding guidewires for delivery.

As further illustrated in FIG. 2B, the infusion tube 36 extends within the catheter lumen 24 toward the catheter distal portion 20. The infusion tube 36 is coupled with and in fluid communication with the fluid emanator 44. For example, the infusion lumen 38 is in fluid communication with the jet orifices 46 through an interior of the fluid emanator 44 by way of a fluid passage 62 extending around the fluid emanator 44 and providing high pressure fluid to each of the jet orifices 46. When assembled, the fluid emanator 44 is optionally positioned distal relative to the inflow orifice 26. In an example, the fluid emanator 44 is positioned distal relative to the inflow orifice 26 and proximal relative to the pivot cylinder 30.

As discussed herein, the fluid emanator 44 includes one or more jet orifices 46 configured to direct one or more fluid jets through the catheter lumen 24 from near the inflow orifice 26 toward the outflow orifice 28. As shown in FIG. 2B, the fluid emanator 44 includes one or more jet orifices 46 directed in a proximal direction toward the catheter proximal portion 18 (as shown in FIG. 1). Stated another way, the jet orifices 46 are positioned on a proximal face 56 of the fluid emanator 44 and are directed within the catheter lumen 24 along the longitudinal axis 60 of the catheter body 16 toward the catheter proximal portion 18 (as shown in FIG. 1).

In an example, the fluid jet emanator 44 is a circular or semi-circular fixture within the catheter body 16. For example, the fluid jet emanator 44 extends around a catheter body interior wall 64 and is engaged with a catheter body interior wall 64 along a fluid emanator perimeter surface 58. The fluid jet emanator 44 produces fluid jets to create the cross stream flow, as discussed herein, and thereby remove and exhaust thrombus from the vessel. The fluid jet emanator 44 includes one or more jet orifices 46 that direct the one or more fluid jets through the catheter lumen 24. The infusion tube 36 and the fluid jet emanator 44 deliver the pressurized fluid to the distal portion 20 of the catheter body 16 for creation of high velocity fluid jet streams which are directed distally from the fluid jet emanator 52, as discussed herein. In another example, the high velocity fluid jet streams are directed both distally and radially. In yet another example, the high velocity fluid jet streams are directed radially from the emanator and into the vessel directly (e.g., without the inflow and outflow orifices). In one example, the jet orifices 46 are configured to provide a jet flow velocity of within a range of from about 1 to about 500 meters per second (m/s). In another example, the jet orifices 46 are configured to provide the jet flow velocity within a range of from about 1 m/s to about 350 m/s.

In the example shown in FIG. 2A, the treatment portion 34 of the catheter body 16 includes a single outflow orifice 28 that is configured to direct a fluid jet radially away from a longitudinal axis 60 of the catheter body 16 and a single inflow orifice 26 that is configured to direct fluid with thrombus entrained into the catheter lumen 24. For instance, the outflow orifice 28 ensures the fluid jet generated impinges upon thrombus in a vessel surrounding the catheter body 16 and the inflow orifice 26 ensures that the fluid including entrained thrombus is delivered downstream through the catheter lumen 24. As the catheter body 16 is rotated (e.g., the treatment portion 34 rotates about the pivot cylinder 30), the cross stream flow between the inflow and outflow orifices 26, 28 travel the full measure of the vessel and remove the thrombus around the catheter distal portion 20 (or over some portion of the vessel if rotated over an arc less than 360 degrees).

In the example illustrated in FIG. 2A, the treatment portion 34 includes a single outflow orifice 28 and a single inflow orifice 26. In other examples, a plurality of outflow orifices 28 and a plurality of inflow orifices 26 are provided at one or more locations on the catheter body 16 (e.g., radially around the catheter distal portion 20, and the like). A single outflow orifice 28, as shown in FIG. 2A, concentrates the hydrodynamic energy of the infusion fluid to better break up the thrombus.

As illustrated in FIGS. 2A and 2B, the fluid emanator 44 include one or more jet orifices 46 on a proximal face 56 of the fluid emanator 44. In an example, the fluid emanator 44 includes one or more jet orifices 46 on a radial surface, such that the fluid jets generated flow away from the longitudinal axis 60 of the catheter body 16. In that example, the catheter body 16 includes corresponding outflow orifices to deliver the fluid jets directly to the vessel.

In the example illustrated in FIGS. 2A and 2B, the infusion tube 36 is positioned within the catheter lumen 24. In another example, the infusion tube 36 is positioned within a sidewall of the catheter lumen 24. That is, the infusion tube 36 is positioned between the catheter body external surface 42 and the catheter body internal surface 64. The infusion tube 36 is formed from a material such as, but not limited to, stainless steel, a polymer, a Nitinol tube or the like.

FIG. 3A illustrates a partial cross-section of the hydrodynamic catheter 40 in FIGS. 1 and 2. As illustrated in FIG. 3A, the fluid emanator 44 is positioned distal relative to the inlet orifice 26, which is spaced from the outlet orifice 24. In an example, the catheter lumen 24 terminates at a termination point 68. The termination point 68 is proximal relative to a distal tip 66 of the catheter body 16. In an example, the distal tip 66 is a solid structure and includes the pivot cylinder 30 extending from the pivot cylinder inlet 48 to the pivot cylinder outlet 52. The pivot cylinder 30 is eccentrically positioned relative to the longitudinal axis 60 of the catheter body 16. In an example, the pivot cylinder outlet 52 is positioned at the distal end 68 of the distal tip 66.

The infusion lumen 38 is in fluid communication with the jet orifices 46 through the fluid passage 62. A pressurized fluid 74 travels through the infusion lumen 38, to the fluid passage 62, and through the jet orifices 46 to generate fluid jets 74. In an example, the fluid jets 74 are directed proximally within the catheter lumen 24 and form the cross stream, as discussed herein. In an example, the infusion tube 36 is formed within a sidewall 70 of the catheter body 16 such that along the treatment portion 34 of the catheter body 16 the catheter lumen 24 is free from structural obstructions. As illustrated in FIG. 3A, the guidewire 22 is positioned within the pivot cylinder 30 extending from the pivot cylinder inlet 48 to the pivot cylinder outlet 52. In an example, the pivot cylinder 30 is isolated from the catheter lumen 24. Isolating the pivot cylinder 30 from the catheter lumen 24 ensures that the largest overall profile is available for aspiration of thrombus materials through the catheter lumen 24 without interference by a guidewire being positioned within the catheter lumen 24 (e.g., a guidewire being positioned centrally or along a perimeter and within the catheter lumen 24.

As illustrated in FIG. 3A, a portion of the guidewire 22 is adjacent to the catheter external surface 42. As discussed herein, the treatment portion 34 of the catheter body 16, including the inlet and outlet orifices 26, 28 is rotatable around the pivot cylinder 30 between at least a first rotated position and a second rotated position. In the first rotated position, the inflow and outflow orifices 26, 28 are directed in a first direction and the inflow and outflow orifices 26, 28 are positioned in close proximity to a first portion of a vessel. In the second rotated position, the inflow and outflow orifices 26, 28 are directed in a second direction different from the first direction, and the inflow and outflow orifices 26, 28 are positioned in close proximity to a second portion of a vessel different from the first portion of the vessel. Positioning the pivot cylinder 30 eccentrically relative to the longitudinal axis 60 allows for a cross-section area of the treatment delivery footprint that is greater than a cross-section area of the catheter body 16. In other words, a virtual perimeter for the treatment portion 34 of the catheter body 16 is greater than a perimeter of the catheter body 16. Thus, the treatment delivery footprint is increased, which increases the efficiency of the thrombectomy, without increasing the diameter of the catheter.

FIG. 3B illustrates a cross-section of the hydrodynamic catheter 40 in FIG. 3A along lines 3B-3B. As illustrated in FIG. 3B, the guidewire 22 is positioned externally to the catheter lumen 24 and eccentrically with respect to the longitudinal axis 60. In an example, the guidewire 22 is positioned adjacent to the catheter external surface 42 along at least the treatment portion 34 of the catheter body 16. Minimizing the structural obstructions (e.g., a guidewire)

between at least inflow and outflow orifices 26, 28 conserves energy (fluid velocity, pressure and the like) allowing for enhanced thrombectomy procedures. For example, by removing the guidewire 22 from the center of the catheter lumen 24, at least adjacent to the inflow and outflow orifices 26, 28 the area within the catheter lumen 24 available for fluid flow during thrombectomy increases thereby enhancing the effectiveness of the hydrodynamic catheter 40. Additionally, providing the guidewire 22 along the catheter body external surface 42 facilitates eccentric rotation of the catheter body 16 (e.g., the treatment portion 34) as the hydrodynamic catheter 40 rotates about the pivot cylinder 30. The eccentric path of the catheter body 16 positions the treatment features (e.g., inlet and outlet orifices 26, 28) in intimate proximity to the thrombus and vessel wall and creates a treatment delivery footprint that is greater than the catheter body 16. Positioning the treatment features in intimate proximity allows the fluid jets to penetrate to the thrombus interior instead of impacting along the exterior of the thrombus and diffusing within the remainder of the vessel.

FIG. 4A illustrates a partial cross-section of another example of a hydrodynamic catheter 76 in accordance with one embodiment of the present disclosure. As illustrated in FIG. 4A, the pivot cylinder 30 is positioned within a sidewall 70 of the catheter body 16. For simplicity, the guidewire 22 is not shown positioned within the pivot cylinder 30. The pivot cylinder 30 is positioned eccentrically relative to the longitudinal axis 60. For example, the pivot cylinder 30 as shown in FIG. 4A is positioned opposite of the inlet and outlet orifices 26, 28 such that an optional maximized distance is formed between the pivot cylinder 30 and the inlet and outlet orifices 26, 28. The maximized spacing facilitates the positioning of the treatment portion 34 intimately with the vessel wall, as the treatment portion 34 rotates about the pivot cylinder 30. In the example illustrated in FIG. 4A, the distal tip 66 of the catheter body 16 includes the catheter lumen 24. That catheter lumen 24 terminates at a termination point 68. However, in other examples, the catheter lumen 24 is open at the distal end of the catheter body 16.

The infusion lumen 38 is in fluid communication with the jet orifices 46 of an emanator 44 through the fluid passage 62. As discussed herein, a pressurized fluid 74 travels through the infusion lumen 38, to the fluid passage 62, and through the jet orifices 46 to generate fluid jets 74 that are directed proximally within the catheter lumen 24 and form the recirculating cross stream with the inflow and outflow orifices 26, 28.

FIG. 4B illustrates a cross-section of the hydrodynamic catheter 76 in FIG. 4A along lines 4B-4B. As illustrated in FIG. 4B, the pivot cylinder 30 including the guidewire lumen is positioned within a wall 70 of the catheter body 16. The pivot cylinder 30 is eccentric relative to the longitudinal axis 60. The hydrodynamic catheter 76 minimizes the structural obstructions (e.g., a guidewire) between at least the inflow and outflow orifices 26, 28 and conserves hydrodynamic energy dedicated to a thrombectomy procedure conducted with the catheter 76. Additionally, positioning the guidewire 22 within the wall 70 of the catheter body 16 allows eccentric rotation of the catheter body 16 as the hydrodynamic catheter 76 rotates about the pivot cylinder 30. The eccentric path of the catheter body 16 positions the treatment features (e.g., inlet and outlet orifices 26, 28) in intimate proximity to the thrombus and vessel wall. In the example illustrated in FIG. 4B, the infusion tube 36 is positioned within the catheter lumen 24. In another example, the infusion tube 36 is positioned within the sidewall 70 of the catheter body 16.

Figure 5:
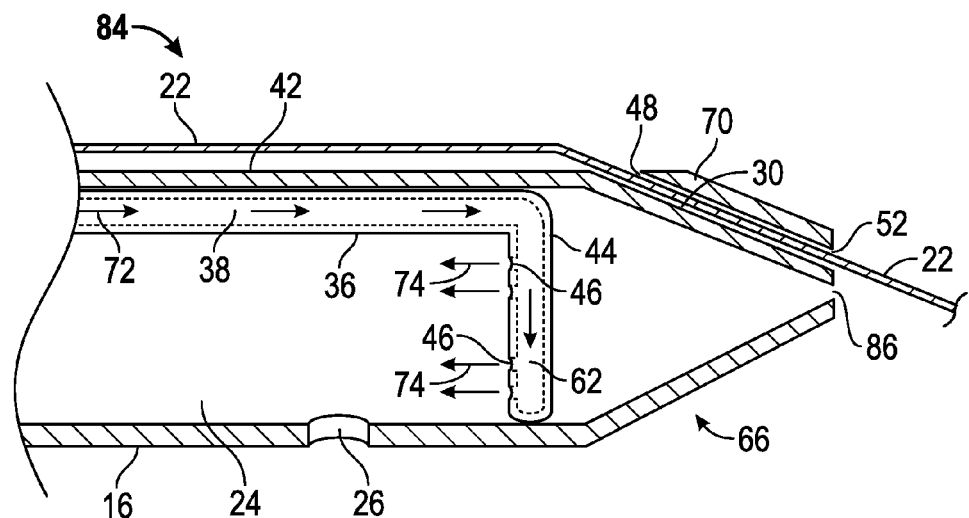
FIG. 5 illustrates a partial cross-section of a portion of another example of a hydrodynamic catheter, in accordance with one embodiment of the present disclosure.

FIG. 5 illustrates a partial cross-section of a portion of another example of a hydrodynamic catheter 84, in accordance with one embodiment of the present disclosure. As illustrated in FIG. 5, the pivot cylinder 30 is positioned within the sidewall 70 of the catheter body 16 along a portion of the catheter body 16 that is distal relative to at least the inflow orifice 26. In an example, the pivot cylinder 30 is positioned within the sidewall 70 of the catheter body 16 along a portion of the catheter body 16 that is distal relative to the fluid emanator 44. The guidewire 22 extends through the pivot cylinder 30 and is positioned adjacent a catheter body external surface 42 along the portion of the catheter body 16 proximal to the pivot cylinder 30. As illustrated in FIG. 5, the catheter lumen 24 extends to a catheter lumen opening 86. However, in other examples, the catheter lumen 24 is closed at the distal end of the catheter body 16, as discussed herein.

Figure 6:
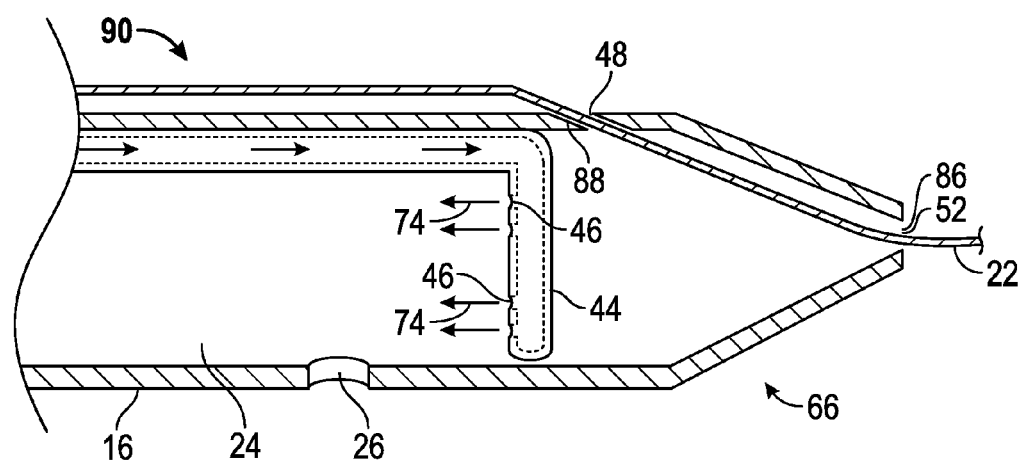
FIG. 6 illustrates a partial cross-section of a portion of another example of a hydrodynamic catheter, in accordance with one embodiment of the present disclosure.

FIG. 6 illustrates a partial cross-section of a portion of another hydrodynamic catheter 90, in accordance with one embodiment of the present disclosure. As illustrated in FIG. 6, the pivot cylinder 30 is a virtual pivot cylinder that is formed between the pivot cylinder opening 48 and the pivot cylinder outlet 52. The pivot cylinder inlet 48 includes a ramped surface 88 to facilitate the insertion of the guidewire 22. In the example illustrated in FIG. 6, the pivot cylinder outlet 52 corresponds to the catheter lumen opening 86.

The hydrodynamic catheters 40, 76, 84, and 90 illustrated in FIGS. 1-6 minimize structural obstructions (e.g., the guidewire) within the catheter lumen 24 between at least the inflow and outflow orifices 26, 28 by positioning the pivot cylinder inlet 48 distal relative to at least one of the inflow orifice 26 and the fluid emanator 44.

Figure 7:
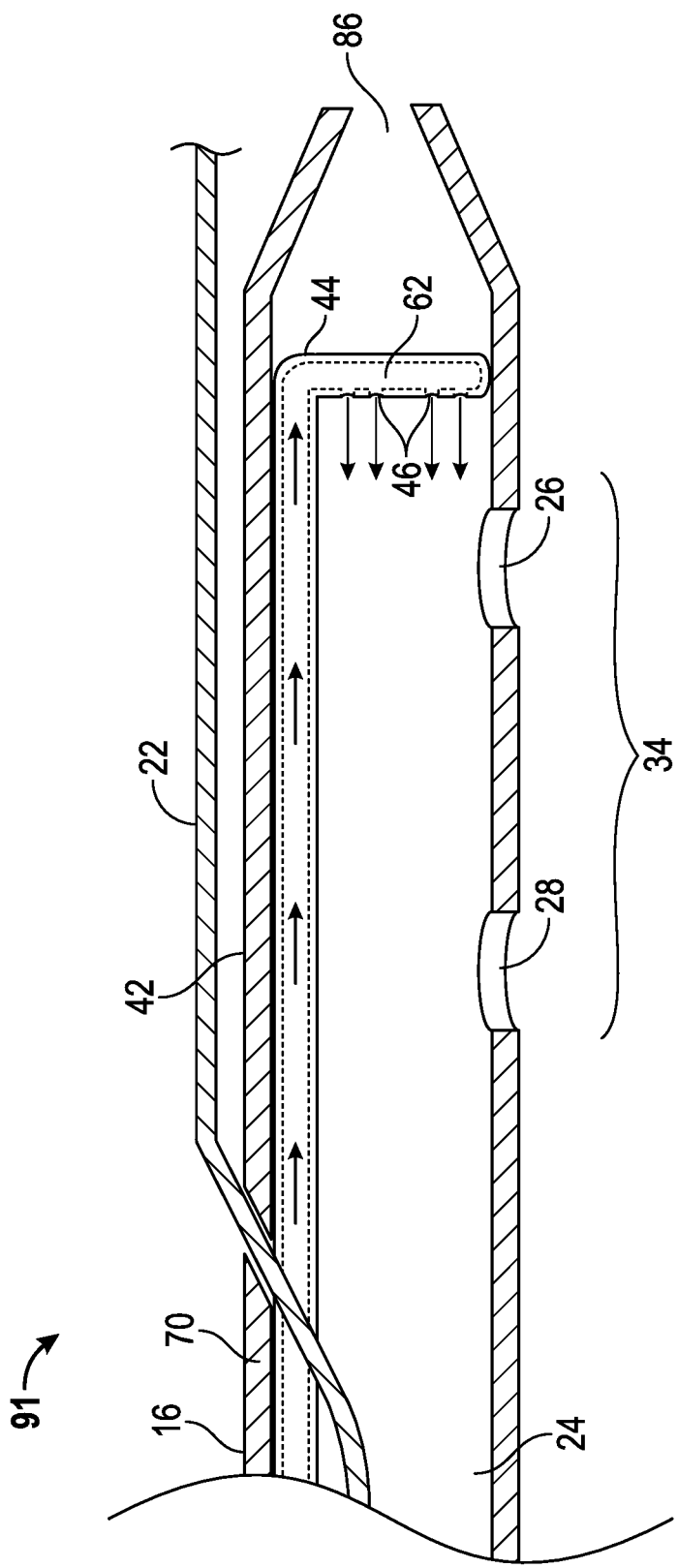
FIG. 7 illustrates a partial cross-section of a portion of another example of a hydrodynamic catheter, in accordance with one embodiment of the present disclosure.

FIG. 7 illustrates a partial cross-section of a portion of another example of a hydrodynamic catheter 91, in accordance with one embodiment of the present disclosure. The hydrodynamic catheter 91 illustrated in FIG. 7 minimizes structural obstructions (e.g., the guidewire) within the catheter lumen 24 between at least the inflow and outflow orifices 26, 28. In an example shown in FIG. 7, the pivot cylinder 30 is positioned proximal relative to the outlet orifice 28. The pivot cylinder 30 includes the guidewire lumen and extends through the sidewall 70 of the catheter body 16. As illustrated in FIG. 7, the guidewire 22 extends along the catheter body external surface 42 between at least the inlet and outlet orifices 26, 28 thereby minimizing the structural obstructions between the inflow and outflow orifices. The guidewire 22 extends within the catheter lumen 24 at a position distal to at least the outlet orifice 28.

Minimizing the structural obstructions (e.g., between the inflow and outflow orifices 26, 28) conserves energy and allows for enhanced thrombectomy procedures. Additionally, removing the guidewire 22 from the catheter lumen 24 at least between the inflow and outflow orifices 26, 28 allows the hydrodynamic catheters 40, 76, 84, 90, and 91 to be eccentric in their path of travel when rotated about the pivot cylinder 30 including the guidewire 22. The eccentric path of the catheter body 16 positions the treatment features (e.g., inlet and outlet orifices 26, 28) in intimate proximity to the thrombus and vessel wall continuously as the catheter body 16 rotates about the pivot cylinder 30.

Figure 8:
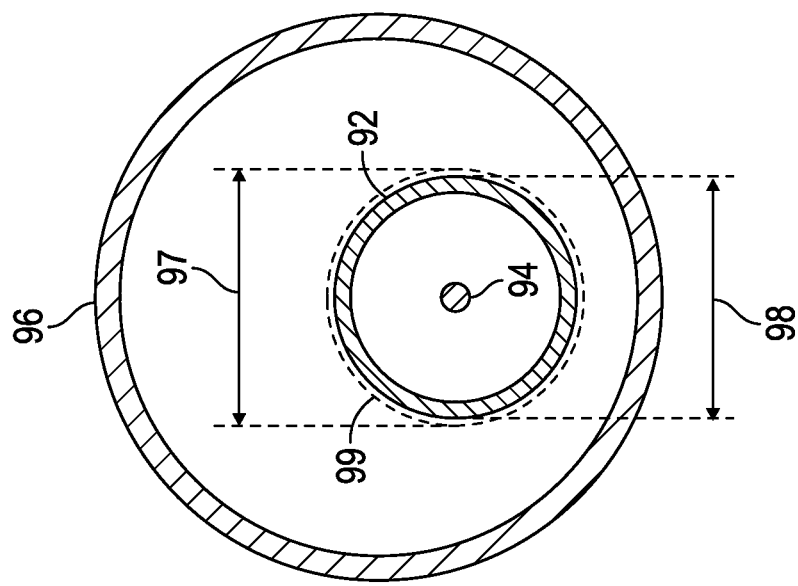
FIG. 8 illustrates a cross-section treatment delivery footprint of a traditional hydrodynamic catheter where the guidewire is concentric with the catheter body.

FIG. 8 illustrates a footprint 99 (in broken line) of a traditional hydrodynamic catheter 96 where a guidewire 94 is substantially concentric with a catheter body 92. As the catheter body 92 rotates about the guidewire 94, the cross-sectional footprint 99 is substantially the same as the cross-sectional area of the catheter body 92. As such, a diameter 98 of the catheter body 92 equals a diameter 97 of the cross-sectional footprint area 99. Rotation of the catheter body 92 about the guidewire 94 during a thrombectomy procedure provides a treatment delivery footprint within the vessel 96 that is substantially similar to the diameter of the catheter body 92. As the thrombectomy is conducted and thrombus is dislodged, remaining organized thrombus is positioned further away from the centrally located catheter body 92. The catheter body 92 illustrated in FIG. 8 is accordingly repeatedly reciprocated and translated laterally as best able with the catheter to further remove thrombus. Accordingly, intimate contact if at all possible requires extensive movement and traversing of the catheter. Additionally, having the guidewire 94 positioned in the path of the indirect cross-path fluid jet streams diminishes and or decreases the strength of the thrombectomy procedure, thereby decreasing the effectiveness of the procedure.

Figure 9:
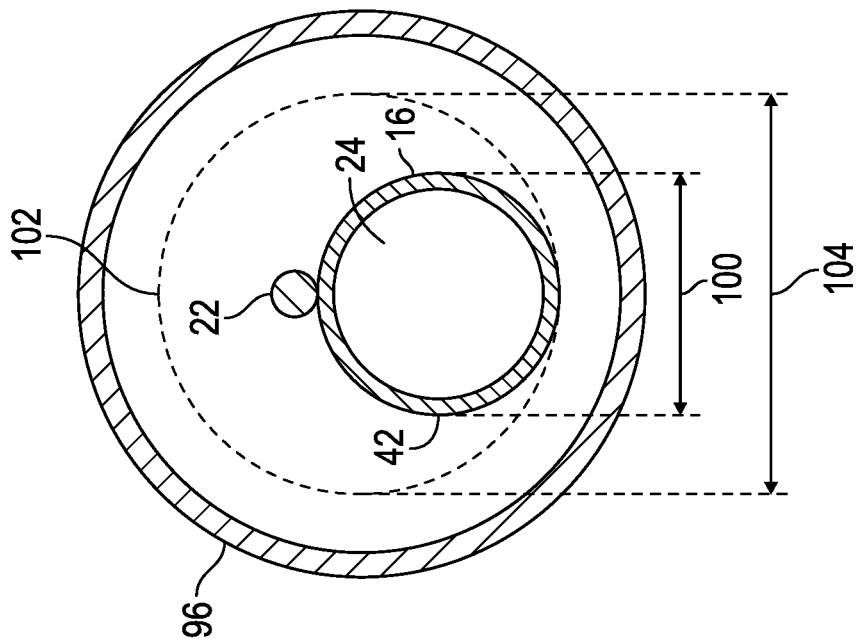
FIG. 9 illustrates an expanded footprint of the hydrodynamic catheter of FIG. 3A, in accordance with one embodiment of the present disclosure.

FIG. 9 illustrates a cross-section treatment delivery footprint 102 of the hydrodynamic catheter 40 of FIG. 3A, in accordance with one embodiment of the present disclosure. The cross-section treatment delivery footprint 102 is taken at a point between the inflow and outflow orifices 26, 28 in FIG. 3A. As illustrated in FIG. 9, the guidewire 22 is positioned along an external surface 42 of the catheter body 16 and is eccentric relative to the catheter lumen 24. As the catheter body 16 rotates about the guidewire 22, a cross-section treatment delivery footprint 102 area formed by the rotation is greater than the cross-sectional area of the catheter body 92. The eccentric positioning of the guidewire 22 provides a cross-sectional footprint area diameter 104 that is approximately twice as large as a catheter body diameter 100. In the example where the guidewire 22 is positioned adjacent the catheter external surface 42, the cross-sectional footprint area diameter 104 is greater than twice the catheter body diameter 100. Accordingly, the treatment delivery footprint 102 of the catheter body 16 within the vessel 96 is increased relative to the configuration shown in FIG. 8 with the guidewire 94 positioned concentrically with a catheter body 92 having an equal diameter (that is the diameter 98 shown in FIG. 8 equals the diameter 100 shown in FIG. 9). In the example illustrated in FIG. 9, the guidewire 22 is positioned along the catheter body external surface 42. In the embodiments described herein with the guidewire 22 positioned within the wall 70 of the catheter body 16 (as illustrated in FIGS. 4A & 4B) a cross-sectional footprint area of those embodiments is greater than the cross-sectional area of the catheter body.

The treatment delivery footprint of the catheter body 16 within the vessel is increased (as illustrated in FIG. 9) with the pivot cylinder 30 as previously described herein relative to the configuration including a guidewire positioned concentrically with a catheter body (as illustrated in FIG. 8). Rotation of the catheter body 16 about the guidewire 22 (positioned within the pivot cylinder 30) during a thrombectomy procedure provides a treatment delivery footprint diameter 102 within the vessel 96 that is greater than the diameter 100 of the catheter body 16. As the thrombectomy procedure is conducted and thrombus is dislodged, the catheter body 16 (e.g., the treatment portion) as illustrated in FIG. 9 maintains intimate contact between the remaining thrombus along the vessel wall and the inlet and outlet orifices of the treatment portion. For example, the portions of the catheter positioned radially away from the guidewire 22, when rotated, are moved into intimate proximity relative to the thrombus and the vessel wall. Accordingly, any catheter treatment features provided at the treatment portions are similarly positioned in intimate proximity to the thrombus and vessel wall. During rotation, the treatment features maintain their intimate proximity to the thrombus and vessel wall.

Figure 10:
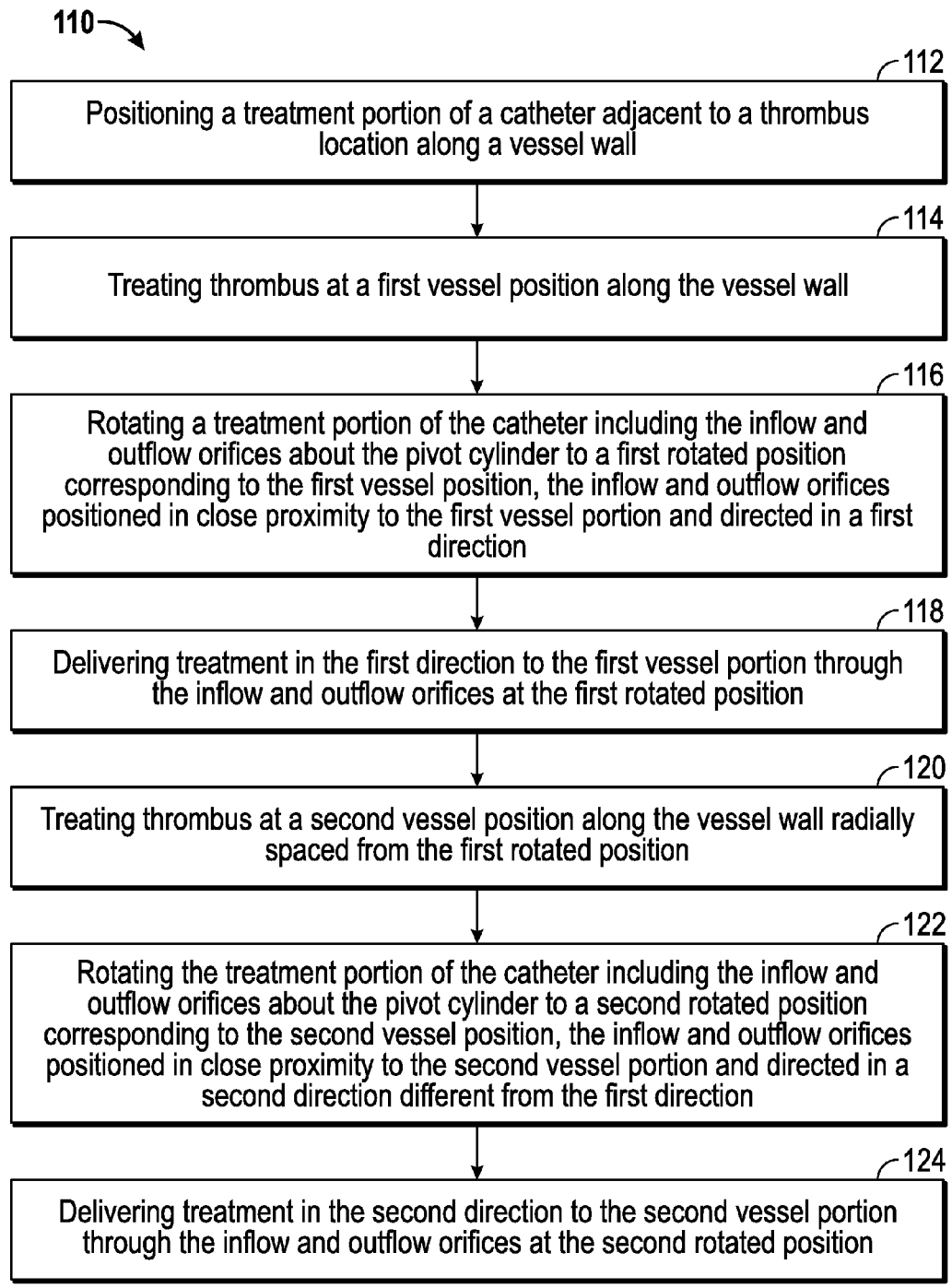
FIG. 10 is a flow chart of a method, in accordance with one embodiment of the present disclosure.

FIG. 10 is a flow chart of a method 110, in accordance with one embodiment of the present disclosure. At 112, a treatment portion of a catheter is positioned adjacent to a thrombus location along a vessel wall. For example, any of the hydrodynamic catheters 40, 76, 84, 90, and 91 as shown in FIGS. 1-7, are used in the method 110. In an example, the hydrodynamic catheter 40 includes a treatment portion 34 including an inflow orifice 26 and an outflow orifice 28, where the outflow orifice 28 is spaced from the inflow orifice 26. The hydrodynamic catheter 40 includes a pivot cylinder 30 eccentrically mounted relative to a catheter longitudinal axis 60, where the pivot cylinder includes a guidewire lumen.

At 114, the thrombus at a first vessel position along the vessel wall is treated. At 116, treating the thrombus at the first vessel position includes rotating a treatment portion of the catheter including the inflow and outflow orifices about the pivot cylinder to a first rotated positioned corresponding to the first vessel position, where the inflow and outflow orifices are positioned in close proximity to the first vessel portion and directed in a first direction. For example, the treatment portion 34 (including the inflow and outflow orifices 26, 28) of the catheter body 16 is rotated about the pivot cylinder 30 to the first vessel position. In an example, rotating the treatment portion 34 of the catheter body 16 to the first rotated position includes rotating the treatment portion 34 of the catheter body 16 about the guidewire 22 received within the pivot cylinder 30. The treatment portion 34 of the catheter body 16 is in intimate proximity to the thrombus deposit along the first vessel wall as the inlet and outlet orifices 26, 28 are positioned opposite from the pivot cylinder 30.

As 118, treating the thrombus at the first vessel position includes delivering treatment in the first direction to the first vessel portion through the inflow and outflow orifices 26, 28 at the first rotated position. In an example, delivering treatment includes moving a fluid under pressure through an infusion tube into a fluid jet emanator. For example, the fluid 72 is moved under pressure through the infusion tube 36 (e.g., within the infusion lumen 38) into the fluid jet emanator 44. The one or more jet orifices 46 generates fluid jets 74 and direct the fluid jets 74 through the catheter lumen 24 from near the inflow orifices 26 toward the outflow orifice 28. The fluid jets 74 generate the cross stream flow that is able to deliver fluid to the vessel through the outlet orifice 28 and draw fluid with thrombus entrained therein into the catheter lumen 24 through the inflow orifice 26.

At 120, the thrombus at a second vessel position along the vessel wall radially spaced from the first vessel position is treated. At 122, treating the thrombus at the second vessel position includes rotating the treatment portion of the catheter (including the inflow and outflow orifices) about the pivot cylinder to a second rotated position corresponding to the second vessel position. For example, the treatment portion 34 including the inflow and outflow orifices 26, 28 is rotated about the pivot cylinder 30 to a second vessel position. The inflow and outflow orifices 26, 28 are positioned in close proximity to the second vessel portion and directed in a second direction different from the first direction.

In an example, rotating the treatment portion 34 of the catheter body 16 to the first and second rotated positions generates a cross-sectional footprint area 102 larger than a cross-sectional area of the catheter body, as shown in FIG. 9. Additionally, rotating the treatment portion 34 of the catheter body 16 to the first and second rotated positions generates a circular cross-sectional footprint area having a footprint diameter 104 approximately twice as large as a catheter body diameter 100. Therefore the cross-sectional treatment delivery footprint area is increased, while maintaining the relatively small diameter of the catheter, as compared to the vessel.

At 124, treating the thrombus at the second vessel position includes delivering treatment in the second direction to the second vessel portion through the inflow and outflow orifices at the second rotated position. In an example, fluid 72 is moved under pressure through the infusion tube 36 (e.g., within the infusion lumen 38) into the fluid jet emanator 44. The one or more jet orifices 46 generates fluid jets 74 and direct the fluid jets 74 through the catheter lumen 24 from near the inflow orifices 26 toward the outflow orifice 28 at the second vessel portion. The fluid jets 74 generate the cross stream flow that is able to deliver fluid to the vessel at the second vessel position through the outlet orifice 28 and draw fluid with thrombus entrained therein into the catheter lumen 24 through the inflow orifice 26. In an example, the second vessel position is approximately 180 degrees from the first vessel position. In another example, the catheter 16 is rotated approximately 360 degrees within the vessel.

During use, the hydrodynamic catheters described herein are inserted into a vessel using a guidewire, for example. The catheter distal portion 20 is navigated through the vasculature and placed adjacent to a thrombus location. The fluid delivery device 10 (as illustrated in FIG. 1) is set to deliver pressurized fluid within a range of from about 10 pounds per square inch (psi) to about 5000 psi. Examples of the fluid delivery device 10 are described in Thor et al., U.S. Pat. No. 7,935,077, entitled "THROMBECTOMY CATHETER DEPLOYMENT SYSTEM" and Bonnette et al., U.S. Pat. No. 6,676,627, entitled "CROSSFLOW THROMBECTOMY CATHETER AND SYSTEM", which are hereby incorporated herein by reference in their entirety.

As discussed herein, the outlet orifice 28 and the one or more fluid orifices 46 are configured by way of shape and size to provide a fluid jet having desired flow characteristics (e.g., velocity and flow rate) configured to remove and macerate thrombus. The fluid control module is associated with the fluid delivery source for controlling fluid flows delivered by the fluid delivery system. In an example, the fluid delivery system includes a user-input control section for interfacing with computer hardware/software (i.e., electronic memory) of the fluid control module.

In an example, the aspirator 8 is coupled to the catheter body 16 and configured to apply a vacuum to remove the fluid and entrained thrombus in the catheter lumen 24. When the aspirator 8 is turned on, the fluid with entrained thrombus enters the catheter lumen through the inlet orifice 26 and is directed toward the catheter proximal end 18 (as shown in FIG. 1) and into a collection container of the aspirator.

In an example, method 110 includes positioning the treatment portion of the catheter within an interior cavity of a filter. For example, the treatment portion 34 of catheter 91 (illustrated in FIG. 7) is positioned distal relative to the pivot cylinder 30. In other words, the pivot cylinder 30 is positioned proximal to at least the outlet orifice 28. In an example, the catheter 91 is combined with a filter and positioned within the interior of the filter such that the treatment portion 34 of the catheter 91 removes material caught within the filer. For example, the hydrodynamic catheter 91 is fed onto a guidewire used for a filter system. As discussed herein, the hydrodynamic catheter 91 is able to rotate about the guidewire and the treatment portion 34 of the hydrodynamic catheter 91 is able to remove material caught within the filter.

FIG. 11A illustrates a partial cross-section of the hydrodynamic catheter 40 in FIGS. 1-3 positioned within a lumen 130 of a vessel 132 including thrombus 134. The hydrodynamic catheter 40 includes the catheter body 16 having the pivot cylinder 30 positioned distal relative to at least one of the fluid jet emanator 44, the outflow orifice 28, and the inflow orifice 26. As shown in FIG. 11A, the inflow and outflow orifices 26, 28 (e.g., the treatment portion 34) is in a first rotated position within the vessel 132 such that the inflow and outflow orifices 26, 28 are directed in a first direction 136. The inflow and outflow orifices 26, 28 are positioned in close proximity to a first portion of a vessel including the thrombus. The first portion of the vessel is treated by delivering the fluid jets via the outflow orifice 28 and having the fluid with entrained thrombus 134 enter the catheter lumen 24 via the inflow orifice 26.

FIG. 11B illustrates a partial cross-section of the hydrodynamic catheter 40 in FIGS. 1-3 positioned within the lumen 130 of the vessel 132 including the thrombus 134. The hydrodynamic catheter 40 in FIG. 11B is positioned at a second rotated position such that the inflow and outflow orifices 26, 28 are directed in a second direction 138 different from the first direction. As illustrated in FIG. 11B, by rotating the inflow and outflow orifices 26, 28 (e.g., the treatment portion 34) about the pivot cylinder 30 ensures that the inflow and outflow orifices are readily maintained in intimate contact with the thrombus at the second (and first) rotated position. As discussed herein, the treatment delivery footprint generated by the hydrodynamic catheter 40 having the guidewire positioned eccentrically relative to a longitudinal axis of the catheter body, is greater than the footprint of the catheter body 16. Thus, the treatment portion 34 of the catheter body is in intimate contact with the thrombus and vessel wall throughout the thrombectomy procedure, thereby increasing the efficiency of the procedure while at the same time using a relatively small diameter catheter body. Additionally, isolating the guidewire 22 from at least the catheter lumen 24 between the inflow and outflow orifices 26, 28 increases the area within the catheter lumen 24 available for energy transfer thereby increasing the efficiency of the device while maintaining a relatively small catheter perimeter, as compared to the vessel.

Figure 12:
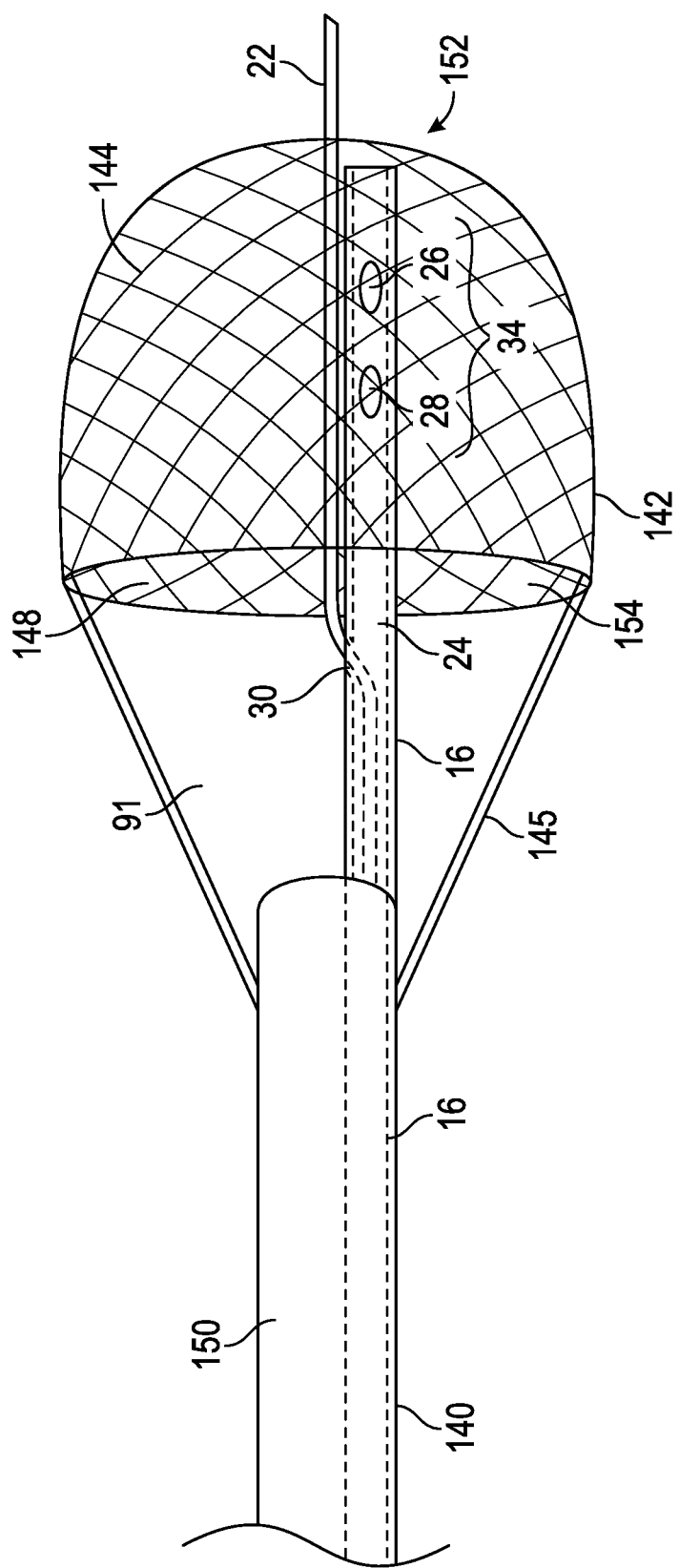
FIG. 12 illustrates a hydrodynamic catheter of FIG. 7 in combination with a filter, in accordance with one embodiment of the present disclosure.

FIG. 12 illustrates a hydrodynamic catheter of FIG. 7 in combination with a filter 142, in accordance with one embodiment of the present disclosure. In an example, a filter catheter 140 and a filter 142 are deployed in a vessel for collection of material within the filter 142. In an example, the filter 142 is a collapsible filter having expanded and retracted configurations. As illustrated in FIG. 12, the filter 142 is in the expanded configuration. The filter 142 includes a filter cavity 148 and a plurality of extension legs 145. The extension legs 145 are coupled to a filter catheter external surface 140. A guidewire 22 through the filter catheter lumen 150 and through a distal end 152 of the filter 142. In an example, the filter 142 is also coupled to the guidewire at the distal end 152. During operation, the filter catheter 140, filter 142, and guidewire 22 are introduced to the vasculature. In one example, the filter catheter 140, filter 142, and guidewire 22 are introduced via a delivery sheath. While the filter catheter 140, filter 142, and guidewire 22 are introduced into the vessel or extended from the delivery catheter, the guidewire 22 and filter catheter 140 move together to maintain the filter 142 in the retracted configuration. When the filter 142 is at a desired location, the guidewire 22 is pulled proximally relative to the filter catheter 140 to transition the filter 142 from the retracted configuration to the expanded configuration (as shown in FIG. 12).

The filter 142 is used to capture material (e.g., thrombus, plaque particulate or the like) and prevent the material from flowing downstream (e.g., past the filter) within the vessel. Over time as the filter mesh 144 collects material, the filter mesh 144 becomes clogged with material such that blood flow is unable to pass through the filter 142. In that instance, it is beneficial to remove the material from the filter mesh 144 without having to remove the entire filter 142. In an example, the hydrodynamic catheter 91 is used to remove the material caught within the filter 142. In an example, the hydrodynamic catheter, as described in FIG. 7, is inserted over the guidewire 22. The catheter body 16 includes the treatment portion 34 having the inflow and outflow orifices 26, 28. In an example, the guidewire 22 enters the catheter body 16 at the pivot cylinder 30, which is positioned proximal relative to at least the outflow orifice 26. The treatment portion 34 of the catheter body 16 is positioned within the filter cavity 148. As discussed herein, the catheter body 16 cooperates with the infusion tube 36 and the fluid emanator 44 (as shown in FIG. 7) to generate a cross stream recirculating flow between the inflow and outflow orifices 26, 28. The recirculating flow enters the vessel and the filter cavity 148 and engages and dislodges the particulate material caught in the filter 142. Fluid with entrained material enters the catheter lumen 24 through the inflow orifice 26 (described above) and is directed toward a proximal end of a catheter. As the catheter body 24 rotates about the guidewire 22, the treatment portion 34 of the catheter body 16 is positioned in intimate contact with, in this example, an interior filter surface 154 over any arc as desired (e.g., through 360 degrees) to remove the material collected by the filter mesh 142.

VARIOUS NOTES & EXAMPLES

Each of these non-limiting examples can stand on its own, or can be combined in any permutation or combination with any one or more of the other examples Example 1 can include subject matter such as a hydrodynamic catheter system. The hydrodynamic catheter system includes a catheter body with a catheter lumen extending from a proximal catheter portion to a distal catheter portion, an infusion tube extending within the catheter body from the catheter proximal portion toward the catheter distal portion, the infusion tube is configured for coupling with a fluid source near the catheter proximal portion, an inflow orifice at a first location along a catheter body perimeter, an outflow orifice at a second location along the catheter body perimeter spaced from the first location, a fluid jet emanator in fluid communication with the infusion tube, the fluid jet emanator including one or more jet orifices, the one or more jet orifices configured to direct one or more fluid jets through the catheter lumen from near the inflow orifice toward the outflow orifice, and a pivot cylinder at a third location along the catheter body perimeter, the third location distal relative to one or more of the fluid jet emanator, the inflow orifice, or the outflow orifice. At least a treatment portion of the catheter body including the inflow and outflow orifices is rotatable around the pivot cylinder between at least first and second rotated positions, where in the first rotated position the inflow and outflow orifices are directed in a first direction, and the inflow and outflow orifices are positioned in close proximity to a first portion of a vessel, and in the second rotated position the inflow and outflow orifices are directed in a second direction different from the first direction, and the inflow and outflow orifices are positioned in close proximity to a second portion of a vessel different from the first portion of the vessel.

Example 2 can include, or can optionally be combined with the subject matter of Example 1, to optionally include where a pivot cylinder inlet is radially spaced around the catheter body from the inflow orifice and the outflow orifice.

Example 3 can include, or can optionally be combined with the subject matter of Example 1 or 2, to optionally include the catheter lumen terminates at a termination point, the termination point proximal relative to a distal tip of the catheter body.

Example 4 can include, or can optionally be combined with the subject matter of one or any combination of Examples 1 through 3 to optionally include a pivot cylinder outlet at a fourth location, the fourth location positioned at a distal end of the distal tip, the fourth location distal relative to the pivot cylinder inlet.

Example 5 can include, or can optionally be combined with the subject matter of one or any combination of Examples 1 through 4, to optionally include where the pivot cylinder outlet is at a non-parallel orientation to the pivot cylinder inlet.

Example 6 can include, or can optionally be combined with the subject matter of Examples 1 through 5 to optionally include where the pivot cylinder is isolated from the catheter lumen.

Example 7 can include, or can optionally be combined with the subject matter of Examples 1 through 6 to optionally include where the fluid jet emanator is coupled with the high infusion tube.

Example 8 can include, or can optionally be combined with the subject matter of Examples 1 through 7 to optionally include where the one or more jet orifices are positioned on a proximal face of the fluid jet emanator, and the one or more jet orifices are configured to direct the one or more fluid jets proximally.

Example 9 can include, or can optionally be combined with the subject matter of Examples 1 through 8 to optionally include where the treatment portion of the catheter body rotatable around the pivot cylinder is rotatable 360 degrees.

Example 10 can include, or can optionally be combined with the subject matter of Examples 1 through 9 to optionally include where the treatment portion of the catheter body rotatable around the pivot cylinder has a cross-sectional footprint area larger than a cross-sectional area of the catheter body.

Example 11 can include, or can optionally be combined with the subject matter of Examples 1 through 10 to optionally include where the treatment portion of the catheter body rotatable around the pivot cylinder has a circular cross-sectional footprint area having a footprint diameter approximately twice as large as a catheter body diameter.

Example 12 can include, or can optionally be combined with the subject matter of Examples 1 through 11 to optionally include where the pivot cylinder is eccentrically spaced from a longitudinal axis of the catheter body.

Example 13 can include subject matter such as a hydrodynamic catheter system. The hydrodynamic catheter system includes a hydrodynamic catheter. The hydrodynamic catheter includes a catheter body with a catheter lumen extending from a proximal catheter portion to a distal catheter portion and an infusion tube extending within the catheter body from the catheter proximal portion toward the catheter distal portion, a treatment portion of the catheter body including an inflow orifice at a first location along a catheter body perimeter, and an outflow orifice at a second location along the catheter body perimeter spaced from the first location, a fluid jet emanator in fluid communication with the infusion tube, the fluid jet emanator including one or more jet orifices, the fluid jet emanator configured to direct one or more fluid jets through the catheter lumen from near the inflow orifice toward the outflow orifice, a pivot cylinder adjacent to the treatment portion and distal relative to one or more of the fluid jet emanator, the inflow orifice, or the outflow orifice.

Example 14 can include, or can optionally be combined with the subject matter of Examples 1 through 13 to optionally include where the treatment portion is rotatable around the pivot cylinder to form a treatment footprint, the inflow and outflow orifices are positionable along a footprint perimeter of the treatment footprint, and the footprint perimeter is in close proximity to a vessel wall, and a treatment footprint area is larger than a cross-sectional area of the catheter body.

Example 15 can include, or can optionally be combined with the subject matter of Examples 1 through 14 to optionally include where in a first rotated position the inflow and outflow orifices are directed in a first direction, and the inflow and outflow orifices are positioned in close proximity to a first portion of a vessel, and wherein in a second rotated position the inflow and outflow orifices are directed in a second direction different from the first direction, and the inflow and outflow orifices are positioned in close proximity to a second portion of a vessel different from the first portion of the vessel.

Example 16, can include, or can optionally be combined with the subject matter of Examples 1 through 15 to optionally include where a pivot cylinder inlet is radially spaced around the catheter body from the inflow orifice and the outflow orifice.

Example 17 can include, or can optionally be combined with the subject matter of Examples 1 through 16 to optionally include a pivot cylinder outlet at a distal end of the distal tip, and the pivot cylinder outlet is distal relative to the pivot cylinder inlet.

Example 18 can include, or can optionally be combined with the subject matter of Examples 1 through 17 to optionally include where the pivot cylinder outlet is at a non-parallel orientation to the pivot cylinder inlet.

Example 19 can include, or can optionally be combined with the subject matter of Examples 1 through 18 to optionally include where the pivot cylinder is positioned outside of the catheter lumen.

Example 20 can include, or can optionally be combined with the subject matter of Examples 1 through 119 to optionally include where the pivot cylinder extends along a catheter body exterior.

Example 21 can include, or can optionally be combined with the subject matter of Examples 1 through 20 the pivot cylinder is eccentrically spaced from a longitudinal axis of the catheter body.

Example 22 can include, or can optionally be combined with the subject matter of Examples 1 through 21 to optionally include where in a first rotated position the inflow and outflow orifices are directed in a first direction, and the inflow and outflow orifices are positioned in close proximity to a first portion of a vessel, and wherein in a second rotated position the inflow and outflow orifices are directed in a second direction different from the first direction, and the inflow and outflow orifices are positioned in close proximity to a second portion of a vessel different from the first portion of the vessel.

Example 23 can include, or can optionally be combined with the subject matter of Examples 1 through 22 to optionally include a fluid source, and a fluid delivery device coupled with the fluid source and the infusion tube configured to provide a fluid under a user-controllable pressure through the one or more jet orifices.

Example 24 can include subject matter such as a method for using a hydrodynamic catheter. The method includes positioning a treatment portion of a catheter adjacent to a thrombus location along a vessel wall, the treatment portion of the catheter including an inflow orifice and an outflow orifice, the outflow orifice spaced from the inflow orifice, the catheter including a pivot cylinder eccentrically mounted relative to a catheter longitudinal axis. The method includes treating thrombus at a first vessel position along the vessel wall. Treating thrombus at the first vessel position along the vessel wall includes rotating a treatment portion of the catheter including the inflow and outflow orifices about the pivot cylinder to a first rotated position corresponding to the first vessel position, the inflow and outflow orifices positioned in close proximity to the first vessel portion and directed in a first direction, and delivering treatment in the first direction to the first vessel portion through the inflow and outflow orifices at the first rotated position. The method includes treating thrombus at a second vessel position along the vessel wall radially spaced from the first vessel position including rotating the treatment portion of the catheter including the inflow and outflow orifices about the pivot cylinder to a second rotated position corresponding to the second vessel position, the inflow and outflow orifices positioned in close proximity to the second vessel portion and directed in a second direction different from the first direction, delivering treatment in the second direction to the second vessel portion through the inflow and outflow orifices at the second rotated position.

Example 25 can include, or can optionally be combined with the subject matter of Examples 1 through 24 to optionally include where rotating the treatment portion of the catheter to the first and second rotated positions includes rotating the treatment portion of the catheter about a guidewire received within the pivot cylinder.

Example 26 can include, or can optionally be combined with the subject matter of Examples 1 through 25 to optionally include where rotating the treatment portion of the catheter to the first and second rotated positions generates a cross-sectional footprint area larger than a cross-sectional area of the catheter body.

Example 27 can include, or can optionally be combined with the subject matter of Examples 1 through 26 to optionally include where rotating the treatment portion of the catheter to the first and second rotated positions generates a circular cross-sectional footprint area having a footprint diameter approximately twice as large as a catheter body diameter.

Example 28 can include, or can optionally be combined with the subject matter of Examples 1 through 27 to optionally include moving a fluid under pressure through an infusion tube into a fluid jet emanator, the infusion tube and the fluid jet emanator positioned within a catheter lumen, the fluid jet emanator including one or more jet orifices configured to direct a fluid jet through the catheter lumen from near the inflow orifice toward the outflow orifice.

Example 29 can include, or can optionally be combined with the subject matter of Examples 1 through 26 to optionally include drawing fluid with thrombus entrained therein into the inflow orifice in each of the first and second rotated positions, and moving the fluid and the entrained thrombus toward the catheter proximal portion through the catheter lumen.

Example 30 can include, or can optionally be combined with the subject matter of Examples 1 through 29 to optionally include positioning the treatment portion of the catheter within an interior cavity of a filter, the pivot cylinder proximal relative to the outflow orifice.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A thrombectomy catheter, comprising:
   a tubular member including a proximal portion, a distal portion and a lumen extending therein;
   a tapered distal tip positioned along the distal portion of the tubular member, the distal tip including an aperture in communication with the lumen of the tubular member;
   an inflow orifice positioned at a first location along the distal portion of the tubular member;
   an outflow orifice positioned at a second location along the distal portion of the tubular member;
   a fluid jet emanator positioned within the lumen of the tubular member, the fluid jet emanator including one or more jet orifices, the one or more jet orifices configured to direct one or more fluid jets in a proximal direction; and
   a guidewire passageway formed in the sidewall of the tapered distal tip, the guidewire passageway including a proximal guidewire opening that is open to the outer surface of the tubular member and a distal guidewire outlet, the passageway positioned distal of the inflow orifice, the outflow orifice and the fluid jet emanator, the guidewire passageway configured to orient the catheter such that it forms an eccentric path of travel when the catheter is rotated about a guidewire extending through the guidewire passageway;
   wherein the proximal guidewire opening defines the proximalmost guidewire opening of the guidewire passageway, and wherein the proximal guidewire opening is distal of both the inflow orifice and outflow orifice.

2. A hydrodynamic catheter, comprising:
   a catheter body including a catheter lumen extending from a proximal catheter portion to a distal catheter portion;
   an infusion tube extending within the catheter body;
   an inflow orifice positioned along a catheter body;
   an outflow orifice positioned proximal the inflow orifice;
   a fluid jet emanator in fluid communication with the infusion tube, the fluid jet emanator including one or more jet orifices, the one or more jet orifices configured to direct one or more fluid jets through the catheter lumen from near the inflow orifice toward the outflow orifice; and
   a pivot cylinder extending through a sidewall of the catheter body, the pivot cylinder including a pivot cylinder inlet that is open to the outer surface of the tubular member, the pivot cylinder inlet positioned proximal a pivot cylinder outlet, and wherein the pivot cylinder inlet is positioned distal the inflow orifice and the outflow orifice; and wherein the inflow and outflow orifices are rotatable around the pivot cylinder between at least first and second rotated positions:
- in the first rotated position the inflow and outflow orifices are directed in a first direction, and the inflow and outflow orifices are positioned in close proximity to a first portion of a vessel, and
- in the second rotated position the inflow and outflow orifices are directed in a second direction different from the first direction, and the inflow and outflow orifices are positioned in close proximity to a second portion of a vessel different from the first portion of the vessel.

3. The hydrodynamic catheter of claim 2, wherein the pivot cylinder inlet is radially spaced around the catheter body from the inflow orifice and the outflow orifice.

4. The hydrodynamic catheter of claim 3, wherein the catheter lumen terminates at a termination point, the termination point proximal relative to a distal tip of the catheter body.

5. The hydrodynamic catheter of claim 2, wherein the pivot cylinder outlet is at a non-parallel orientation to the pivot cylinder inlet.

6. The hydrodynamic catheter of claim 2, wherein the pivot cylinder is configured to direct a guidewire from a position inside the catheter lumen to a position outside the catheter body.

7. The hydrodynamic catheter of claim 2, wherein the catheter body rotates around the pivot cylinder so as to create a treatment area having a cross-sectional footprint area larger than a cross-sectional area of the catheter body.

8. The hydrodynamic catheter of claim 2, wherein the catheter body rotates around the pivot cylinder so as to create a treatment area having a circular cross-sectional footprint area having a footprint diameter approximately twice as large as an outer diameter of the catheter body.

9. The hydrodynamic catheter of claim 2, wherein the pivot cylinder is eccentrically spaced from a longitudinal axis of the catheter body.

* * * * *